US010357237B2

(12) United States Patent
De Mayo et al.

(10) Patent No.: US 10,357,237 B2
(45) Date of Patent: Jul. 23, 2019

(54) BOOT FOR LIMB AND ANKLE TRAUMA SURGERY USING MODULAR DISTRACTOR

(71) Applicant: INNOVATIVE MEDICAL PRODUCTS, INC., Plainville, CT (US)

(72) Inventors: Edward De Mayo, Greenbrae, CA (US); Timothy Blackwell, Jupiter, FL (US)

(73) Assignee: INNOVATIVE MEDICAL PRODUCTS, INC., Plainville, CT (US)

( * ) Notice: Subject to any disclaimer, the term of this patent is extended or adjusted under 35 U.S.C. 154(b) by 534 days.

(21) Appl. No.: 15/132,237

(22) Filed: Apr. 18, 2016

(65) Prior Publication Data

US 2016/0287238 A1 Oct. 6, 2016

Related U.S. Application Data

(63) Continuation-in-part of application No. 15/098,609, filed on Apr. 14, 2016, which is a continuation of
(Continued)

(51) Int. Cl.
| | |
|---|---|
| *A61B 17/02* | (2006.01) |
| *A61B 50/15* | (2016.01) |
| *A61G 13/00* | (2006.01) |
| *A61G 13/10* | (2006.01) |
| *A61G 13/12* | (2006.01) |

(Continued)

(52) U.S. Cl.
CPC ........... *A61B 17/025* (2013.01); *A61B 50/15* (2016.02); *A61F 5/04* (2013.01); *A61G 13/0036* (2013.01); *A61G 13/101* (2013.01); *A61G 13/125* (2013.01); *A61G 13/1245* (2013.01); *A61B 2017/00477* (2013.01); *A61B 2017/0212* (2013.01); *A61B 2017/0268* (2013.01)

(58) Field of Classification Search
CPC ... A61B 17/60; A61B 17/66; A61B 2017/681; A61B 17/025; A61B 2017/0268; A61B 2017/0275
See application file for complete search history.

(56) References Cited

U.S. PATENT DOCUMENTS

| | | | | |
|---|---|---|---|---|
| 3,020,909 A | * | 2/1962 | Stevens | A61G 13/0036 5/623 |
| 4,526,355 A | * | 7/1985 | Moore | A61G 13/0063 5/624 |

(Continued)

*Primary Examiner* — Anu Ramana
(74) *Attorney, Agent, or Firm* — Damian Wasserbauer, Esq.; Wasserbauer Law LLC

(57) ABSTRACT

A boot assembly apparatus, system and method for elevating the patient's limb when using a manual distractor unit is mounted upon a support frame attached to an operating table side rail. A foot strap is attached to the boot assembly apparatus and to the patient's ankle with a patient's knee support pad, extending from the distractor unit, is positioned under the patient's knee to provide traction to the patient's ankle, which is secured to the support frame. The boot assembly apparatus may be formed with a plurality of attachment points for the foot strap so as to provide improved access to the ankle area with advantages of allowing additional types of procedures a surgeon could perform on the patient and/or the ability of the surgeon to access the ankle area and lower leg.

4 Claims, 5 Drawing Sheets

Related U.S. Application Data application No. 13/134,238, filed on Jun. 3, 2011, now Pat. No. 9,314,272.

(51) Int. Cl.
*A61F 5/04* (2006.01)
*A61B 17/00* (2006.01)

(56) References Cited

U.S. PATENT DOCUMENTS

| | | | | |
|---|---|---|---|---|
| 5,020,525 A | * | 6/1991 | Ewing | A61F 5/04 602/27 |
| 5,025,802 A | * | 6/1991 | Laico | A61G 13/12 128/875 |
| 5,290,220 A | * | 3/1994 | Guhl | A61F 5/04 128/882 |

* cited by examiner

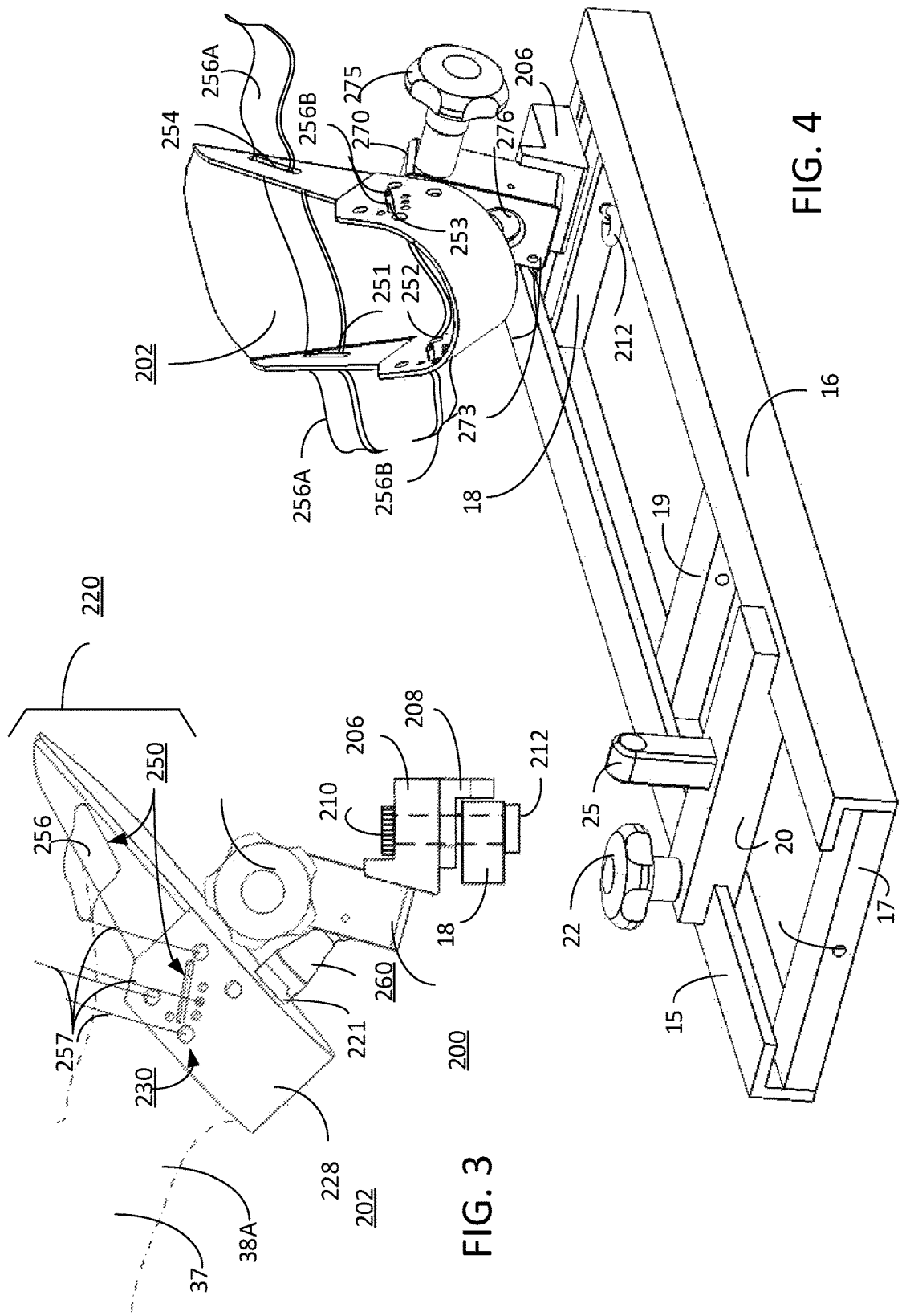

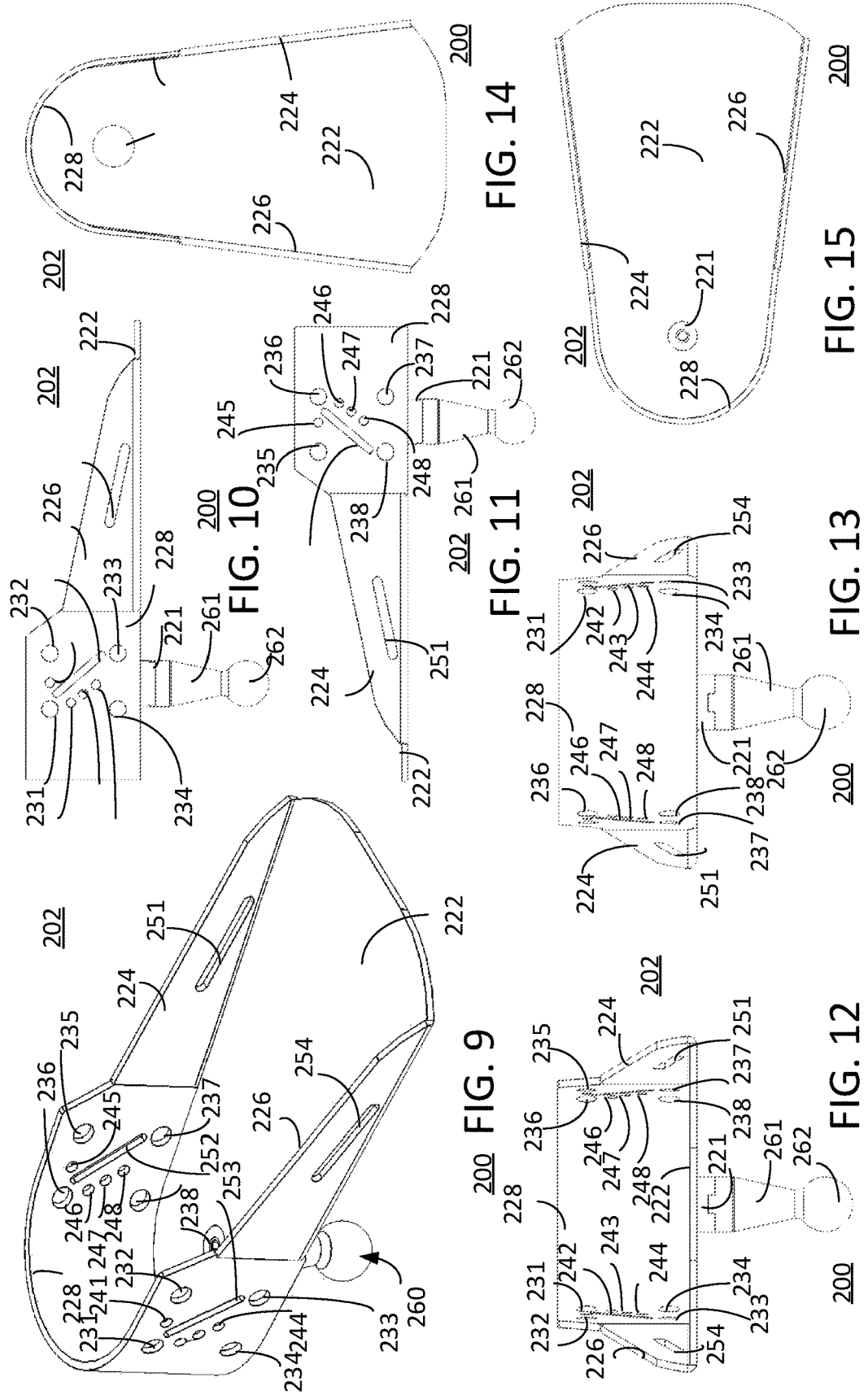

BOOT FOR LIMB AND ANKLE TRAUMA SURGERY USING MODULAR DISTRACTOR

CROSS-REFERENCE TO RELATED APPLICATION

This application is a continuation-in-part of U.S. patent application Ser. No. 15/098,609 filed Apr. 14, 2016, entitled "Modular Distractor System For Use In Surgery" which is a continuation of and claims the benefit of U.S. Pat. No. 9,314,272 issued Apr. 19, 2016 entitled "Modular distractor for use in ankle surgery", that are incorporated here by reference in their entirety.

FIELD OF THE INVENTION

The present invention relates to distraction in a surgical procedure and, more particularly, to boot assembly, system and method for holding an ankle and distracting at a knee to provide improved access in surgical procedures involving the ankle area and lower leg.

BACKGROUND OF THE INVENTION

Methods currently available for ankle distraction procedures generally restrain the patient's leg and apply controlled pressure to the ankle for the required traction.

U.S. Pat. No. 5,290,220 entitled "Non-Invasive Distraction System for Ankle Arthroscopy" and U.S. Pat. No. 5,025,802 entitled "Surgical Holding Apparatus for Distracting Ankle" both describe applying such traction to the ankle directly.

The use of such equipment in the vicinity of the ankle could impair circumferential access to the patient's foot and ankle, during surgery, under some circumstances.

It has been shown that by restraining the patient's ankle with a simple strap and applying pressure to the underside of the patient's knee, the ankle can be distracted while allowing the surgeon complete access to the ankle in all directions.

One purpose of the instant invention is to provide a simple means of securing the patient's ankle while applying pressure to the underside of the patient's knee for such ankle arthroscopy by means of a manual distractor which can also be used for other joint arthroscopic surgery.

SUMMARY OF THE INVENTION

One end of a manual distractor unit used in various joint distraction surgery is mounted to one end of a support frame attached to an operating table side rail. A patient's knee support pad, at an opposite end of the distractor unit, is positioned under the patient's knee to provide traction to the patient's ankle, which is secured by a strap to the support frame.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Description of the Preferred Embodiments, which is to be read in association with the accompanying drawings, which are incorporated in and constitute a part of this specification, show certain aspects of the subject matter disclosed herein and, together with the description, help explain some of the principles associated with the disclosed implementations, wherein:

FIG. 3 is a side perspective view of the boot assembly after attachment of the support frame to an operating table shown in FIG. 1 for surgical procedures involving the lower limb, tibia, or ankle surgical procedures with a portion of the patient's limb depicted in phantom thereon according to an embodiment of the present invention;

FIG. 4 is a perspective schematic view of the boot assembly and support without the modular distractor removed according to an embodiment of the invention;

FIG. 9 is a perspective view of the boot assembly according to an embodiment of the invention;

FIG. 10 is a side view illustrating the boot assembly of the invention;

FIG. 11 is a side view illustrating the boot assembly of the invention;

FIG. 12 is a front view illustrating the boot assembly of the invention;

FIG. 13 is a rear view illustrating the boot assembly of the invention;

FIG. 14 is a bottom view illustrating the boot assembly of the invention; and

FIG. 15 is a top view illustrating the boot assembly according to the present invention.

DESCRIPTION OF THE PREFERRED EMBODIMENTS

Figure 1:
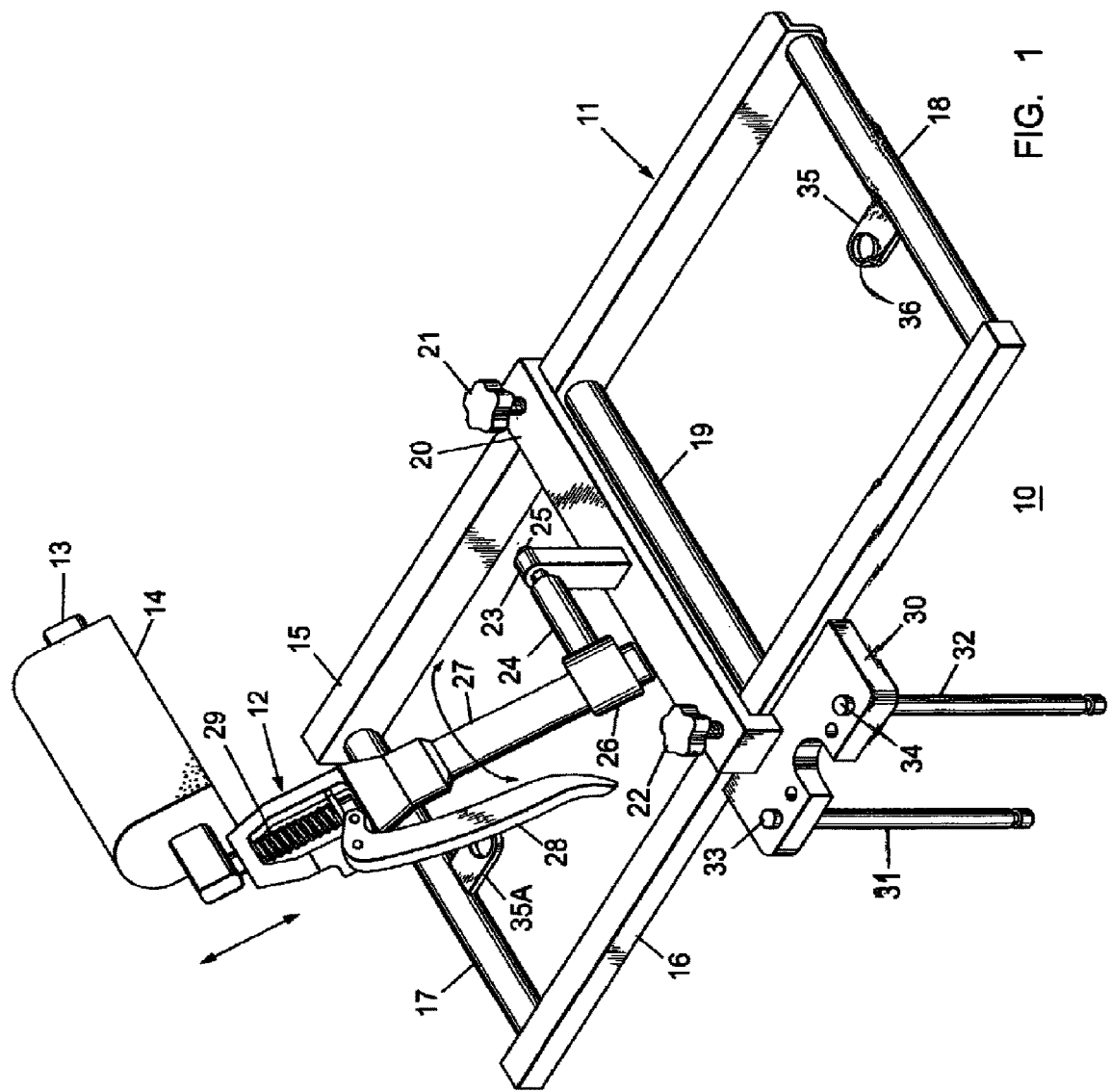
FIG. 1 is front perspective view of the modular patient's ankle distractor unit in accordance with the invention prior to attachment to the operating table.

Non-limiting embodiments of the present invention will be described below with reference to the accompanying drawings, wherein like reference numerals represent like elements throughout. While the invention has been described in detail with respect to the preferred embodiments thereof, it will be appreciated that upon reading and understanding of the foregoing, certain variations to the preferred embodiments will become apparent, which variations are nonetheless within the spirit and scope of the invention.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "some embodiments", "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

The drawings featured in the figures are provided for the purposes of illustrating some embodiments of the present invention, and are not to be considered as limitation thereto. Term "means" preceding a present participle of an operation indicates a desired function for which there is one or more embodiments, i.e., one or more methods, devices, or apparatus for achieving the desired function and that one skilled in the art could select from these or their equivalent in view of the disclosure herein and use of the term "means" is not intended to be limiting.

Figure 6:
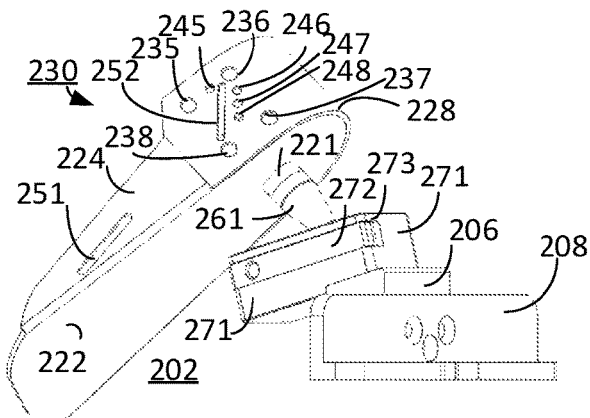
FIG. 6 is a rear view illustrating the hinge of the boot assembly according to the invention.
Figure 7:
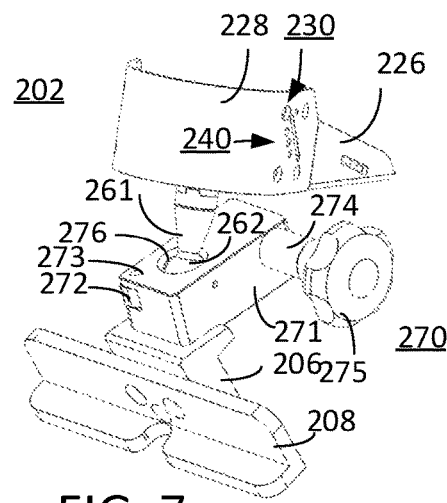
FIG. 7 is a bottom view illustrating the hinge of the boot assembly according to the invention.
Figure 8:
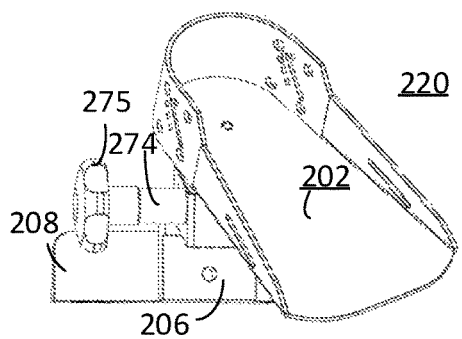
FIG. 8 is a perspective view of the boot assembly and support according to an embodiment of the invention.

As used herein the term "boot" refers to a boot holder for a foot, leg, and/or part of the limb of a leg. A half boot for holding a foot is illustrated, for example, in FIGS. 3-4, and 8-14. A full boot for holding a leg is illustrated, for example, in FIGS. 5-7.

Figure 5:
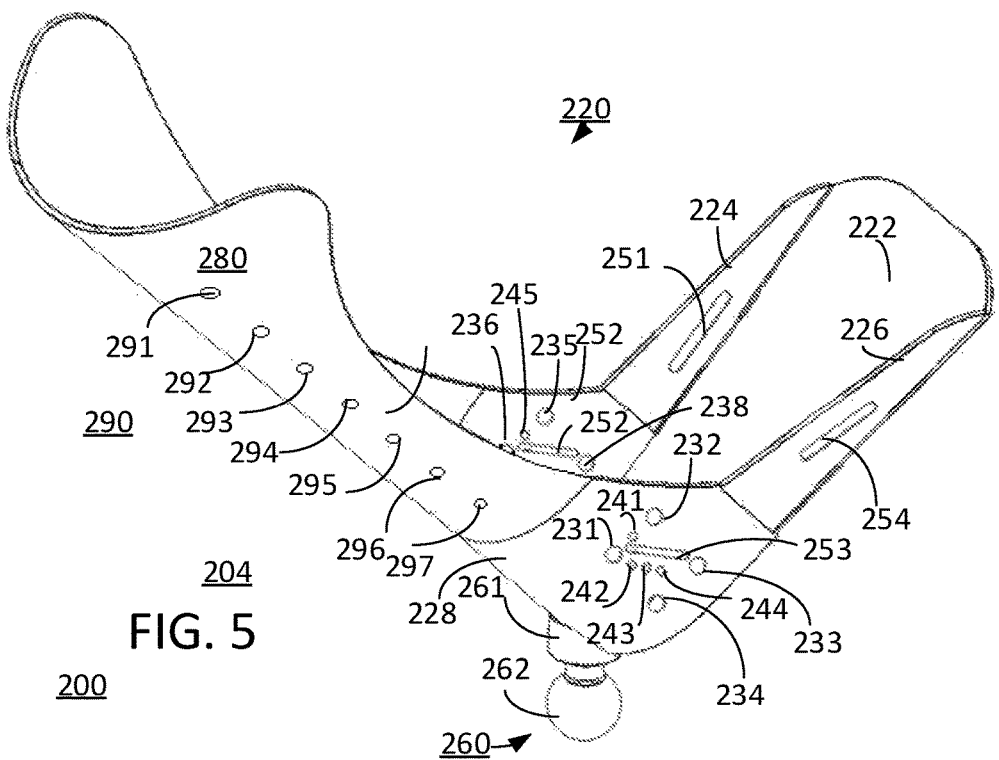
FIG. 5 is a side view illustrating an limb and boot assembly according to the invention.

Referring to FIGS. 1 through 15, an boot assembly apparatus, system and method 200 for use in surgical procedures with the ankle distractor for restraining the patient's ankle with a simple strap attached to the boot assembly apparatus 200 and to the patient's ankle while applying pressure to the underside of the patient's knee by an distractor assembly 12 for improved access to the overall leg including the ankle for during arthroscopic surgery or other surgical procedure at the ankle and tibia area. The boot assembly 200 features access holes 232 provide access during trauma surgeries of the leg (i.e. multiple fractures, in the tibia and ankle, etc.) where multiple fractures need to be secured and then set. For example, referring to FIGS. 3 and 4, a patient's leg 37 and patient's ankle 38A is secured in the boot assembly 200 by a strap 256, which may be secured in slots 251, 253, and/or by adding another strap 256 in slots 252, 254, or once the bone is set using a guide wire or rod 258 set through the access holes 230 so as to allow removing the strap 256. In addition, as is shown in FIG. 5, a full boot 204 may be utilized when there is a tibial fracture to the leg 37 as well as fractures to the ankle 38A, whereby guide wires 257 and rods 258 may be inserted into access holes 230 depending on which is needed and provides access to the desired anatomical structure, for example, large holes 231, 232, 233, 234, 235, 236, 237, and 238 on the heel portion 228, as well as smaller holes 241, 242, 243, 244, 245, 246, 247, and 248 also formed on the hill portion 228 adjacent strap slots 252, 253, as is shown in FIGS. 9-15. Also as is shown in FIG. 5, access holes 290 such as, for example, holes 291, 292, 293, 294, 295, 296, and 297 will provide access to the anatomical structure of the leg.

Figure 2:
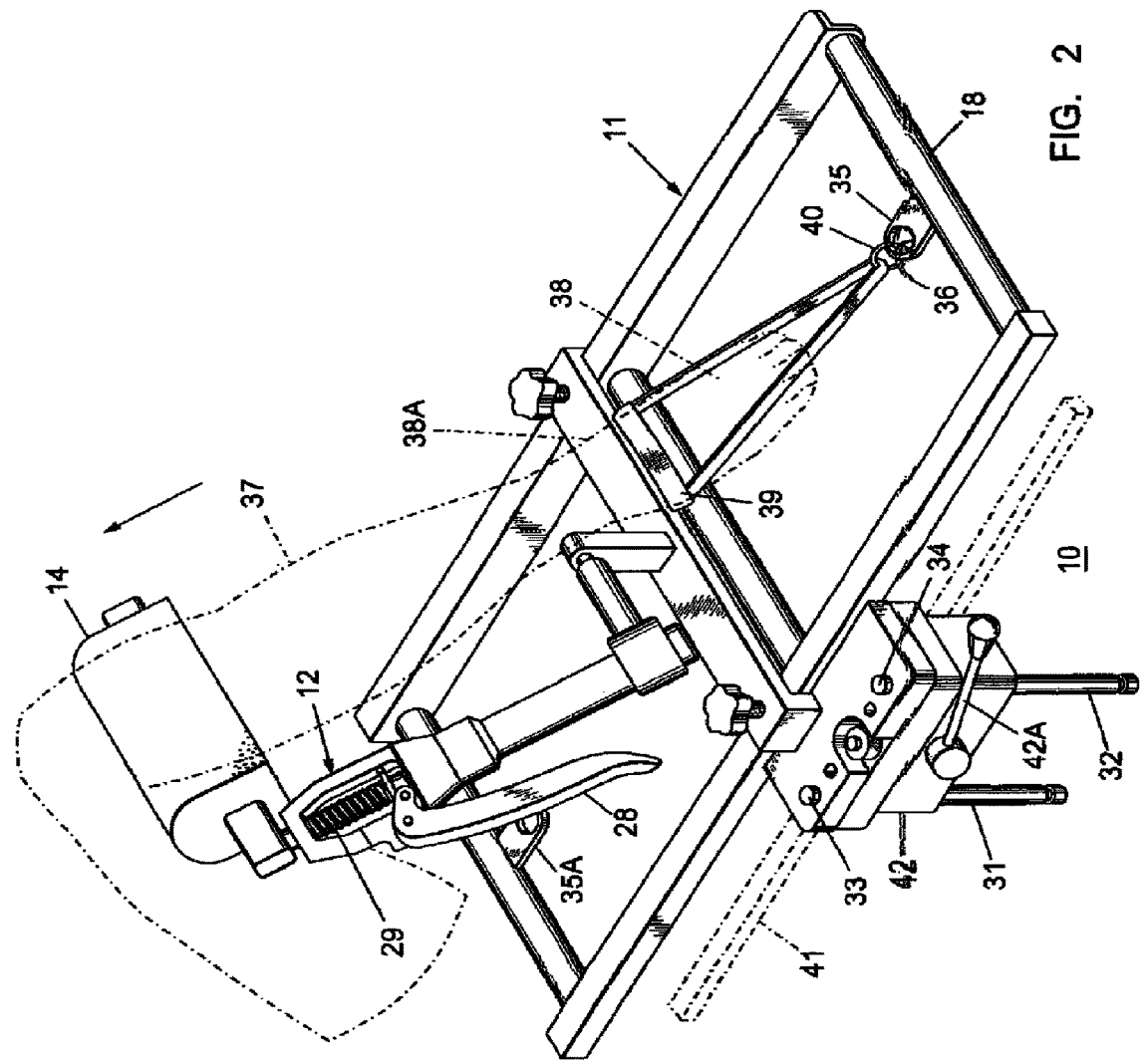
FIG. 2 is a front perspective view of the patient's ankle distractor unit of FIG. 1 after attachment to the operating table with a portion of the patient's limb depicted in phantom thereon.

Referring to FIGS. 1, 2 and 3, the boot assembly apparatus, system and method 200 comprises a base portion 222 with upwardly extending side portions 224, 226 and a heel portion 228, said side and heal portions including a plurality of slots 250 generally, 251, 252, 253, 254 configured to accept a foot strap 260 for securing a patient's foot ankle to one of said pair of first and second end bars of said support frame during the distraction surgery. heel portion includes a plurality of holes 230 on boot 202, and holes 290 on boot 204, configured to provide access to the patient's foot during the distraction surgery The components of the foot assembly 202, and/or boot 204 configured to secure to the support frame 11 comprises a mounting block 206, base bracket 208, and the clamp to 270 which includes body 271 with an arm 272 joined to the body 271 by hinge 273, having a socket 276 formed in said body 271 and arm 272 for receiving the ball 262 therein, the ball 262 may be secured in said socket 276 by fastening the arm 272 to the body 271 by a threaded fastener to 274 and knob 275 whereby the arm 272 is fastened around the ball to 262 on the extension to 261 of the post 260 so as to operably connect the ball 262 in the socket 276. These components may be formed from suitable materials such as surgical grade stainless steel, and other metal alloys.

As shown in FIGS. 1-3, a modular ankle distractor unit 10 includes a support frame 11 and a manual distractor 12, which includes a support bar 13 for the patient support pad 14 for moving the support pad 14 in the up and down directions, as indicated, in combination with the compression spring 29 and the distractor operating handle 28. The manual distractor 12 is described within U.S. patent application Ser. No. 12/001,194 entitled "Non-Invasive Femoral Distractor," which Application is incorporated herein for purposes of reference.

The support frame 11 includes a pair of side bars 15, 16, end bars 17, 18 and center bar 19. A support bar 20 extends between the side bars 15, 16 and is attached thereto by means of threaded knobs 21 and 22. A post 23, upstanding from the support bar 20, is attached to a rod 24 by means of a bolt 25 and the rod 24 is welded to the support collar 26. One end of the manual distractor cylinder 27 is arranged within the support collar 26 whereby the manual distractor 12 can be rotated in the clockwise and counter-clockwise directions, as indicated, by loosening the bolt 25. The plate extension 30 on the end of the support bar 20 includes at a pair of operating table connector posts 31, 32 attached thereto by means of bolts 33 and 34. A tab 35 is attached to the end bar 18 and includes an opening 36 for receiving a clip connector 40 to retain the patient's foot strap 39, as shown in FIG. 2. A similar tab 35A is attached to the end bar 17.

Referring now to FIGS. 2-3, the support frame 11 is depicted attached to an operating table side rail 41 by a side rail clamp 42 and operating handle 42A which engages the operating table connector posts 31, 32. The side rail clamp 42 is similar to that described within U.S. Pat. No. 7,380,299 entitled "Operating Table Support Clamp". To provide ankle distraction, a patient's limb 37 is arranged on the patient support pad 14 and the patient's foot 38 is secured within foot strap 39, which is secured to the end bar 18 by means of the tab 35, clip connector 40 and opening 36, as described earlier. One such foot strap 39 is a Guhl Ankle Distractor Foot Strap obtained from Smith & Nephew Inc. To provide distraction to the patient's ankle 38A, the distractor operating handle 28 on the manual distractor 12 is operated to move the patient support pad 14 and limb 37 in the indicated direction, while the ankle 38A is retained by virtue of the foot strap 39. When the distraction of the ankle 38A is completed, the compression spring 29 allows the support pad 14 to return the limb 37 to the original position upon release of the distractor operating handle 28.

Referring to FIGS. 3-15, a simple and efficient arrangement has been described herein whereby a patient's ankle can be precisely distracted and the leg and/or ankle of the patient may be set in predetermined positions during reconstructive surgeries involving the leg and ankle such as, for example, in trauma where multiple fractures need to be positioned and set while other bones are manipulated and secured in the place. Referring to FIG. 3, certain circumstances require the patient's ankle and/or leg (using the boot 204 as shown in FIG. 5) to be positioned differently so as to access the entire limb leg and the ankle area and drill to the bone, secure a rod to the bone and then treat the fracture by setting the break with screws, pins, plates and other methods. As a result, the present invention provides a half-boot 202 and a full-boot 204 boot assembly apparatus, system and method 200 that may be secured to the frame 11. The boot apparatus 200 is configured to distract at the knee with the limb being positioned at different horizontal angles with respect to the table so as to accommodate the exact position the surgeon has to place the patient in based on the various factors such as, for example the type of fracture, the type of surgery, the type of arthroscopic surgery, patients body and/or limb size with multiple attachment points for the strap 37. For example, in a surgical procedure to reset a tibial fracture with distraction at the knee by the manual distractor unit 12, or to strengthen the tibial fracture with surgical plates and pins, the boot assembly 200 may be used to position the patient's limb substantially horizontal so as to provide improved access for the surgeon. Similarly, in surgical procedures for the ankle area, the boot assembly may be utilized to position the limb in various relative horizontal position so as to properly position the ankle according to the fracture and other factors for improved access to the ankle area when the ankle area is distracted.

In many surgical procedures, this arrangement is adequate to address and have access to the patient's leg area in arthroscopic surgeries and fractures as well as improved access to the area of the ankle. Referring to FIG. 2, according to an embodiment of Applicant's invention, an ankle distractor and strap, system and method is used for restraining the patient's ankle with a simple strap and applying pressure to the underside of the patient's knee, the ankle can be distracted while allowing the surgeon complete access to the ankle in all directions. Such an ankle distractor and strap is described in U.S. patent application Ser. No. 13/134,238 filed Jun. 3, 2011 entitled "Modular distractor for use in ankle surgery," which is incorporated by reference herein in its entirety.

While certain configurations of structures have been illustrated for the purposes of presenting the basic structures of the present invention, one of ordinary skill in the art will appreciate that other variations are possible which would still fall within the scope of the appended claims. Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A modular distractor system for connecting to an operating table for performing surgery on the leg of a patient, comprising:
  a support frame comprising a pair of first and second side bars, a pair of end bars, a support bar operably connected between said first and second side bars, a post extending from said support bar operably connected to a support collar, and a plate extension operably connected to said support bar, said plate extension comprising a pair of connector posts for operably connecting to a side rail clamp attached to the operating table,
  a manual distractor unit comprising a collar portion at one end configured to operably connect to said support collar of said support bar and an adjustable assembly at an opposite end comprising a support bar configured to receive a support pad, a distractor handle and a compression spring, said adjustable assembly configured to move said support pad in combination with a distractor handle and a compression spring, said collar portion configured to provide rotatable adjustment of said manual distractor unit relative to said support frame, said support pad adapted to apply pressure to the popliteal area of a patient's knee when said adjustable assembly unit is extended linearly, said compression spring for moving said support bar thereby returning to an original position after the distraction has been completed;
  a foot assembly for securing to said support frame, said foot assembly comprising a mounting block, a base bracket, and a clamp, said mounting block and base bracket operably connecting said clamp to one of said pair of end bars, said clamp comprising a body with an arm joined to the body by a hinge, and a socket formed in said body and said arm; and
  a boot assembly comprising a base portion with post and ball extending on the underside thereof and a heel portion with post and ball extending on the underside thereof, said ball configured to be received in said socket and secured therein by said clamp, said side and heal portions including a plurality of slots configured to accept a foot strap for securing a patient's foot and/or ankle therein.

2. The distractor system of claim 1 wherein said heel portion includes a plurality of holes configured to provide access to the patient's foot during the distraction surgery.

3. The distractor system of claim 2 said plurality of holes includes large holes and small holes wherein said small holes are configured to receive drills and guide wires, and said large holes are configured to receive drills, rods and/or guide wires therein.

4. The distractor system of claim 1, said boot portion further comprising upwardly extending side portions from said heel portion, said upwardly extending side portions including a plurality of holes configured to provide access to the patient's leg during the distraction surgery.

* * * * *